United States Patent [19]

Ilvento et al.

[11] Patent Number: 5,366,497
[45] Date of Patent: * Nov. 22, 1994

[54] NON-INVASIVE, RADIOLUCENT CARDIAC ELECTRODE

[75] Inventors: Joseph P. Ilvento, Santa Barbara; Bruno T. Bisceglia, Jr., Oceanside; Tim J. Way, Carlsbad, all of Calif.

[73] Assignee: Cardiotronics, Inc., Carlsbad, Calif.

[*] Notice: The portion of the term of this patent subsequent to Oct. 18, 2011 has been disclaimed.

[21] Appl. No.: 860,995

[22] Filed: Mar. 31, 1992

[51] Int. Cl.⁵ ............................................. A61B 5/04
[52] U.S. Cl. ..................................... 607/142; 607/4; 128/653.2
[58] Field of Search ............... 128/639, 640, 798, 783, 128/653.2, 660.07, 661.02, 661.04, 653.1; 607/5, 4

[56] References Cited

U.S. PATENT DOCUMENTS

| | | | |
|---|---|---|---|
| 1,212,541 | 1/1917 | Morse | 128/639 |
| 1,498,059 | 6/1924 | Tyler | 128/639 |
| 1,989,282 | 1/1935 | Kimble et al. | 128/639 |
| 2,536,271 | 1/1951 | Fransen | 128/639 |
| 2,632,447 | 3/1953 | Dobes | 128/421 |
| 3,085,577 | 4/1963 | Berman et al. | 128/639 |
| 3,472,233 | 10/1969 | Sarbacher | 128/639 |
| 3,817,252 | 6/1974 | Maurer | 128/639 |
| 4,030,509 | 6/1977 | Heilman et al. | 128/419 D |
| 4,050,453 | 9/1977 | Castillo et al. | 128/783 |
| 4,187,853 | 2/1980 | Barton et al. | 128/419 P T |
| 4,207,904 | 6/1980 | Greene | 128/798 |
| 4,226,247 | 10/1980 | Hauser et al. | 128/639 |
| 4,239,046 | 12/1980 | Ong | 128/639 |
| 4,243,051 | 1/1981 | Wittemann | 128/639 |
| 4,243,052 | 1/1981 | Bailey | 128/798 |
| 4,257,424 | 3/1981 | Cartmell | 128/641 |
| 4,270,549 | 6/1981 | Heilman | 128/784 |
| 4,291,707 | 9/1981 | Heilman et al. | 128/78 A |
| 4,314,095 | 2/1982 | Moore et al. | 128/419 P |
| 4,370,984 | 2/1984 | Cartmell | 128/640 |
| 4,442,315 | 4/1984 | Segawa | 174/36 |
| 4,539,995 | 9/1985 | Segawa | 128/639 |
| 4,576,170 | 3/1986 | Bradley et al. | 128/419 D |
| 4,674,511 | 6/1987 | Cartmell | 128/640 |
| 4,685,467 | 8/1987 | Cartmell et al. | 128/640 |
| 4,722,354 | 2/1988 | Axelgaard et al. | 128/798 |
| 4,748,983 | 6/1988 | Shigeta et al. | 128/639 |
| 4,765,341 | 8/1988 | Mower et al. | 128/785 |
| 4,800,887 | 1/1989 | Shigeta et al. | 128/639 |
| 4,817,594 | 4/1989 | Juhasz | 128/155 |
| 4,827,932 | 5/1989 | Ideker et al. | 128/419 D |
| 4,846,178 | 7/1989 | Fuxue et al. | 128/419 F |
| 4,893,626 | 1/1990 | Henley et al. | 128/640 |
| 4,938,231 | 7/1990 | Milijasevic et al. | 128/784 |
| 4,955,381 | 9/1990 | Way et al. | 128/419 D |
| 5,148,805 | 9/1992 | Schamberg | 128/640 |

OTHER PUBLICATIONS

Cardiotronics' 510K Premarket Notification for the Model #210 Stealth Defib. Pad, Filed with the FDA on Sep. 27, 1990.

Physio-Control packing and labeling for electrodes, pacing only.

Cardiotronics' 510K Premarket Notification for the Model #310 Stealth-Trode+RF Defibrillation Pads, Filed with the FDA on May 4, 1992.

Primary Examiner—William E. Kamm
Assistant Examiner—Scott M. Getzow
Attorney, Agent, or Firm—Lyon & Lyon

[57] ABSTRACT

A non-invasive radiolucent electrode for stimulating the heart is disclosed. The electrode is configured to include at least one pad having a first surface adapted to contact the patient's skin, and a conductive mesh backing substantially covering a second surface of the pad and configured to be radiolucent.

38 Claims, 2 Drawing Sheets

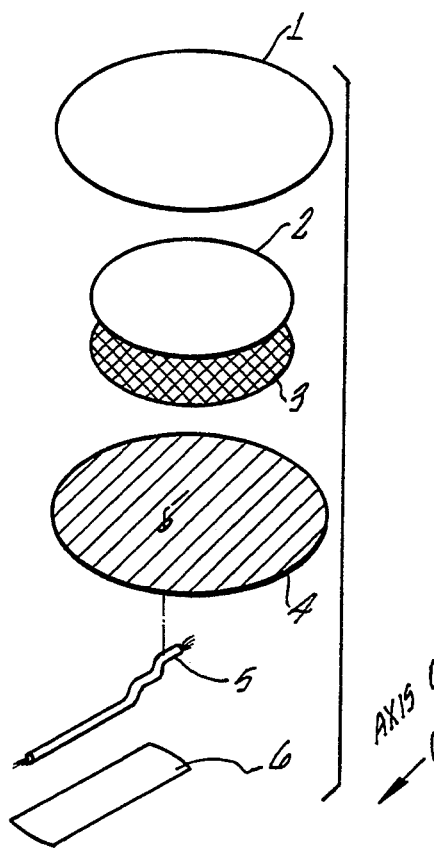
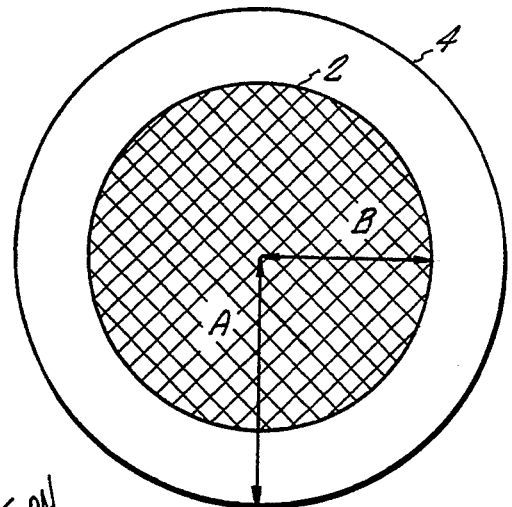
FIG. 2.
FIG. 1.
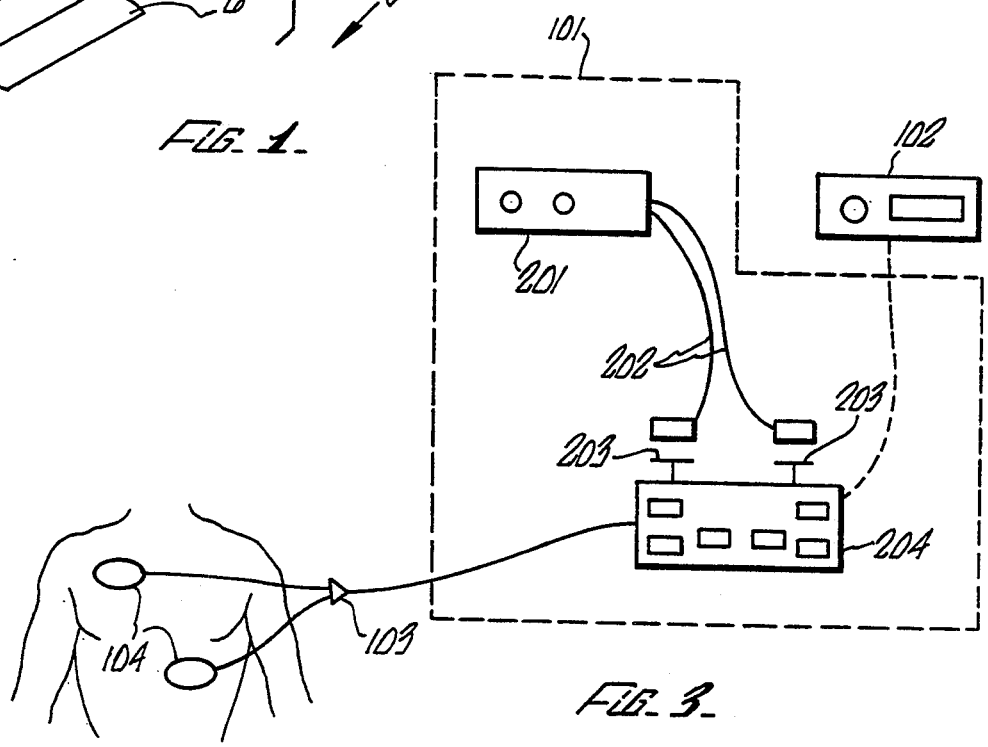
FIG. 3.

NON-INVASIVE, RADIOLUCENT CARDIAC ELECTRODE

BACKGROUND OF THE INVENTION

1. Field of the Invention

This invention relates to a non-invasive cardiac electrode, and more specifically, to a non-invasive, radiolucent cardiac electrode which is capable of conducting energy at a level sufficient for cardiac stimulation.

2. Background Information

Prior art non-invasive electrodes adapted for defibrillating or pacing the heart typically comprise a skin-contacting pad which is laminated to a metal foil conductive backing which in turn is electrically coupled to a source of defibrillating or pacing energy. The purpose of the foil backing is to distribute the energy from the source substantially uniformly over the pad before it is delivered to the patient, thereby eliminating burns or the like which could occur if the energy were to be delivered in a more concentrated fashion. Thus, this foil backing has been viewed as a desirable, and even necessary, component of prior art non-invasive electrodes.

A problem with the prior art foil backing, however, is that it may interfere with the ability to image an aspect of the patient's circulatory system, such as the arteries of the heart, with a fluoroscope or the like, when electrodes containing the prior art backing are positioned on the patient's skin so that multiple cardiac stimulation therapies can be rapidly delivered to the patient should he or she suffer an arrhythmia during the imaging process. The interference may occur because the prior art foil backing typically creates shadows or blemishes in the images of the internal organs, all of which may impede diagnosis of the patient's condition. In the areas of cardiac catheterization, angiography, and angioplasty, for example, the practitioner must be able to see the angiography dye or the catheter to determine the extent of the presence of plaque or other irregularities in the patient's arteries. The foil backing can shadow or block the view of the patient's arteries, thereby leading to an incomplete or improper diagnosis.

Prior art radiolucent electrodes are also available which utilize a conductive rubber backing instead of metal foil. However, these rubber backing materials are suitable only for high impedance external pacing systems. They are not suitable for defibrillation as they have too high an impedance.

As a result, there has been a long-standing but heretofore unmet need for a non-invasive electrode which is radiolucent, and, at the same time, is capable of delivering multiple electrical therapies to a patient, including defibrillation therapies, in the course of an emergency cardiac resuscitation attempt. For the purposes of this disclosure, the term "radiolucent" is defined as the quality of being capable of providing a low enough attenuation of X-irradiation such that body structures such as coronary arteries imaged with intraluminal contrast material may be visualized through the electrode without significant degradation in image quality so as to make the image uninterpretable with respect to luminal irregularities, angioplasty outcome, thrombus formation, or vessel occlusion.

Although several efforts have been directed towards developing such an electrode in the past, none of these efforts have heretofore proven successful. For example, one approach, described more fully in U.S. Pat. Nos. 4,050,453; 4,257,424; 4,370,984; 4,674,511; and 4,685,467, involves forming the conductive element of a monitoring electrode by painting an electrode base with metallic paint or depositing a very thin metallic film on the base. However, this approach could not successfully be utilized in a stimulation electrode which is capable of delivering the level of energy necessary to stimulate the heart, since the thin metallic coating or film would not be capable of conducting the relatively high levels of energy required, typically 300 J or more.

A second approach, described in U.S. Pat. Nos. 4,442,315 and 4,539,995, involves forming the conductive element of the electrode by applying fine particles of an electrically conductive material, such as carbon, to an electrode base. Again, this approach could not successively utilized in a stimulation electrode, since the layer of fine particles would not be capable of conducting the relatively high levels of energy required.

A third approach, described in U.S. Pat. Nos. 4,748,993 and 4,800,887, involves forming the conductive element from a porous carbonaceous material or graphite sheet. A problem with this approach is that the resulting electrode would have too high an impedance when used for defibrillation in that the high levels of energy would cause the electrode to heat up too much.

Accordingly, it is an object of the present invention to provide a radiolucent non-invasive cardiac electrode which is capable of delivering multiple electrical stimulation therapies, including defibrillation, to a patient in the course of an emergency cardiac resuscitation attempt.

SUMMARY OF THE INVENTION

To achieve the foregoing objects, and in accordance with the purpose of the invention as embodied and broadly described herein, there is provided a radiolucent non-invasive electrode for stimulating a patient's heart comprising a pad adapted for contacting the patient's skin over a first surface, a radiolucent conductive mesh backing adapted to contact and substantially cover a second surface of the pad, the backing in one exemplary embodiment comprising a mesh made of stainless steel wires, the mesh having about 15 to 50 wires/inch, and the wires having a diameter of between about 5 to 10 mils, the electrode further comprising means for electrically coupling the radiolucent backing to stimulating means configured to produce electrical impulses adapted to stimulate the patient's heart.

BRIEF DESCRIPTION OF THE DRAWINGS.

FIG. 1 is a drawing showing an exploded view of an electrode incorporating the teachings of the subject invention;

FIG. 2 is a drawing showing the face of an electrode incorporating the teachings of the subject invention;

FIG. 3 is a block diagram of a cardiac system incorporating an electrode of the subject invention;

DESCRIPTION OF THE PREFERRED EMBODIMENT

Figure 4:
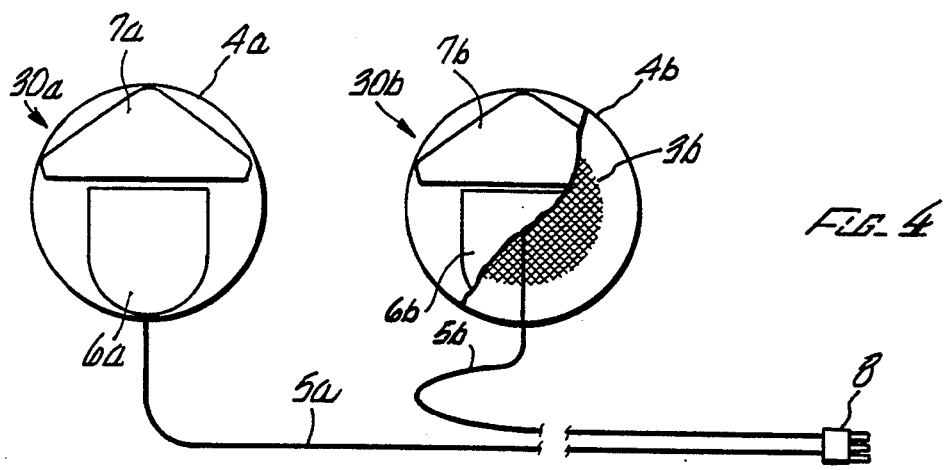
FIG. 4 is a drawing of an electrode pair, where each electrode in the pair incorporates the teachings of the subject invention.

A diagram of an electrode incorporating the teachings of the subject invention is illustrated in FIG. 1. As indicated, the electrode advantageously comprises peelable cover 1, conductive adhesive polymer pad 2, radiolucent backing 3, plastic foam cover 4, insulated wire 5, and wire retainer 6. An object of the electrode is to be radiolucent and still be capable of delivering stimulating electrical impulses to the patient's heart, either pacing pulses or defibrillating pulses, substantially uniformly over the face of the electrode pad.

The peelable cover is advantageously attached to the polymer pad to keep any foreign material off of a first surface of the pad, which surface is adapted to contact the patient's skin, and can be peeled off when the surface of the electrode is about to be applied to the patient's skin.

A second surface of the polymer pad is advantageously adapted to be placed in contact with the radiolucent backing such that the backing substantially covers the second surface. The backing, in turn, is adapted to be placed in contact with the plastic foam cover. The plastic foam cover has a hole in it exposing part of the radiolucent backing, and the insulated wire has an exposed proximal end (with the other end being referred to as the distal end) which is inserted into the hole and electrically coupled to the radiolucent backing, such that the plastic cover is sandwiched between the mesh and the wire.

In the example of FIG. 1, the conductive polymer pad is advantageously 25 mils (1 mil equals 0.001 inch) thick.

The foam backing is advantageously comprised of a rubber closed-cell foam such as MED-416 (available from the FASSON specialty tape division of AVERY INTERNATIONAL). The foam is advantageously closed-cell, i.e., has air pockets completely surrounded by foam, so that no foreign material can get through it. This is to be contrasted with an open-cell material such as a sponge, which allows foreign material such as water to pass completely through it. In addition, the foam backing is advantageously covered with a medical grade adhesive which will enable the foam backing to adhere directly to the radiolucent backing, and to the human body in those areas which extend beyond the polymer pad. In the example of FIG. 1, the foam backing is advantageously 1/16 of an inch (0.062 inches) thick.

In the example of FIG. 2, the overall diameter of the electrode face, identified with A in the figure, is advantageously about 13 cm. (9 cm. for a pediatric electrode), giving rise to an overall area for the electrode face of about 132.67 sq. cm. (63.58 sq. cm. for a pediatric electrode). The diameter of the polymer pad, identified with B in the figure, is advantageously about 10 cm. (6.5 cm. for a pediatric electrode), giving rise to an area of about 78.58 sq. cm. for the pad (33.17 sq. cm. for a pediatric electrode).

Finally, the wire retainer is placed over the hole in the foam backing after the exposed end of the wire has been inserted and electrically coupled to the radiolucent backing. The wire retainer is coated with an adhesive so that it will adhere to the foam backing and reduce strain on the wire.

The pads are preferably composed of an adhesive conductive polymer (also known as a hydrogel) such as Promeon's RG-XX conductive polymer. The RG-XX polymer is advantageous since it is non-hyperallergenic and also has been shown to be a non-irritant to the skin. Conductive polymers are the result of recent, significant advancements in conductive gel technology. A recent article providing more information about conductive polymers is R. Kaner and A. MacDiarmid, Plastics That Conduct Electricity, Scientific American, Vol. 258, No. 2 (Feb. 1988), which is hereby fully incorporated by reference herein as though set forth in full.

In an exemplary embodiment, the polymer pad is comprised of Promeon's RG62-D hydrogel since this particular hydrogel has been found to be compatible with an advantageous embodiment of the radiolucent backing (in which the backing is made of stainless steel—see below). Other hydrogels, such as Promeon's RG63T and RG63B, as well as hydrogels offered by other manufacturers, may be suitable depending on the configuration.

Conductive polymers offer several advantages over existing saline-based gels. First, these polymers have the consistency of rubber, eliminating the smearing problem associated with prior art gels. In addition, because of their rubber-like consistency, these polymers have a longer shelf life than the prior art gels, and they do not leave a residue once they are removed from contact with a patient's skin. Finally, the polymers need not be integrated with a sponge in order to achieve their shape.

Second, the polymers used for the electrodes can be chosen to be inherently adhesive, so that the pads will adhere to a patient's skin over their entire surface area compared with the prior art gel electrodes, which only adhere to the patient's skin at a ring surrounding the pad. As a result, the polymer pads will adhere better, eliminating the problem of burning and electrode movement associated with prior art electrodes.

Third, these polymers have better electrical characteristics than the prior art gels. They are effectively lower in impedance when placed in contact with the patient's skin, since their superior adhesion prevents portions of the electrode from lifting off the patient's skin. Lifting would result in a conductive path to the skin having a high effective impedance at these areas. As a result, less voltage is required to administer a particular stimulating current pulse, and the voltage generator in the cardiac system to which the electrode is integrated, and the entire cardiac system in general, can be made smaller, more compact, and less costly. Also, the polymers, because of their different electrochemistry, will depolarize much faster than prior art gels. In fact, the polymers will typically depolarize in one-half the time it takes for a prior art gel to depolarize.

Fourth, unlike the prior art gels which have a tendency to dry out, conductive polymers dry out less quickly, and can therefore be applied more rapidly, saving much of the critical time spent prior to initiating treatment.

The insulated wire 5 is advantageously 18–20 gauge wire which preconnects the wire to a standard connector for interfacing to a cabling system for coupling the electrode to a defibrillator (see below).

The radiolucent backing will now be described. For purposes here, "radiolucent" is defined to be the quality of producing a low enough attenuation of X-irradiation such that body structures such as coronary arteries imaged with intraluminal contrast material may be visualized through the backing without significant degradation in image quality so as to make the image uninterpretable with respect to luminal irregularities, angioplasty outcome, thrombus formation, or vessel occlusion.

This backing must fulfill three requirements simultaneously which are t cross-purposes. First and foremost, it must be radiolucent. Second, it should be pliable enough to conform to the human body. Third, it must be capable of delivering a sufficient energy for defibrillation, up to 360 Joules, substantially uniformly over the face of the electrode pad.

It has been discovered that all these requirements can simultaneously be met with a conductive mesh backing. In one embodiment, the mesh is made from low-resistance, non-corrosive, pliable metal wires, advantageously stainless steel, although other examples are possible, including aluminum, brass, titanium, or platinum, depending on compatibility with hydrogel. In this embodiment, the diameter of the wires are preferably between about 5 to 10 mils, and most preferably, are less than about 9 mils. Also, in this embodiment, the number of wires per inch, which determines the spacing between the wires, is preferably between about 15 to 50 wires/in, and most preferably between about 20–40 wires/in. Preferably, in this embodiment, all these parameters should be chosen so that the percentage of open space of the mesh is greater than about 50%.

In an exemplary embodiment, it has been found that a stainless steel wire mesh made of wires having a 7.5 mil diameter, and a spacing of 24 wires/in. (resulting in a percentage of open space of about 67.4%) results in a mesh which satisfies all the aforementioned requirements.

Although, as described in U.S. Pat. Nos. 4,030,509; 4,270,549; and 4,291,707, meshes have been used in implantable electrodes in the past, it should be appreciated that the number of wires/inch recommended for these meshes, i.e., about 150 wires/in., is significantly greater than that recommended for the mesh of the subject invention, notwithstanding the teachings of the art, which teach decreasing the percentage of open space, and therefore increasing the number of wires/inch to handle the increased energy requirements of non-invasive electrodes compared to invasive electrodes, i.e., up to 360J as opposed to 30J.

The mesh is advantageously cut into an 8.5 cm. (6 cm. for a pediatric electrode) diameter circle with the rough edge covered with a mylar ring to prevent the mesh from puncturing the other materials in the electrode.

It has been found in practice that an electrode incorporating the mesh backing described above is most appropriate for standby or emergency cardiac situations where defibrillation or countershock is required. In those instances where pacing is also anticipated, it is advantageous to first embed the stainless steel mesh described above in a low conductive rubber (such as Material #CE5745C available from FURON) before applying it to the hydrogel pad. This is because a stainless steel mesh and a hydrogel chosen for compatibility with stainless steel are not in fact compatible with each other under long term pacing conditions. Specifically, the hydrogel which is the lowest impedance and the most suitable for external pacing is not in fact compatible with stainless steel under long-term pacing conditions. Embedding the mesh in a low impedance conductive rubber provides a barrier between the hydrogel and the mesh. This combination of materials differentiates the backing from current electrodes adapted for pacing (discussed in the background section) which are manufactured with a backing made only of conductive rubber.

These electrodes are advantageously disposable, and are bound and packaged together in pairs by a connector system, with the distal ends of the insulated wires 5 emanating from each electrode joined together by a connector. One electrode is typically labeled "Anterior" and the other electrode is typically labeled "Apex." As to packaging, a completed pair of electrodes is advantageously packaged in a poly/foil laminate bag and heat sealed. The purpose of this package is to seal the product to prevent contamination and keep it clean. This product does not require sterilization, so the only requirement of the package is to provide protection and a moisture barrier.

A pair of electrodes is illustrated in FIG. 4, in which compared to previous figures, like elements are referenced with like identifying numerals. The "Anterior" electrode of the pair is referenced with identifying numeral 30a while the "Apex" electrode of the pair is referenced with identifying numeral 30b. The foam backings for the two electrodes are referenced with numerals 4a and 4b, respectively, the mesh backing for the "Apex" electrode, with numeral 3b, the insulated wires for the pair, with numerals 5a and 5b, respectively, and the wire retainers for the pair, with numerals 6a and 6b, respectively. Also shown are labels for each electrode, identified with numerals 7a and 7b, respectively, for use in labelling the electrodes with the manufacturer's name, trade logos, or the like, or for labelling one electrode as "Apex" and the other as "Anterior." Also shown is connector 8 for binding the distal ends of the insulated wires 5a and 5b together and for facilitating connection to a cabelling system.

Figure 5:
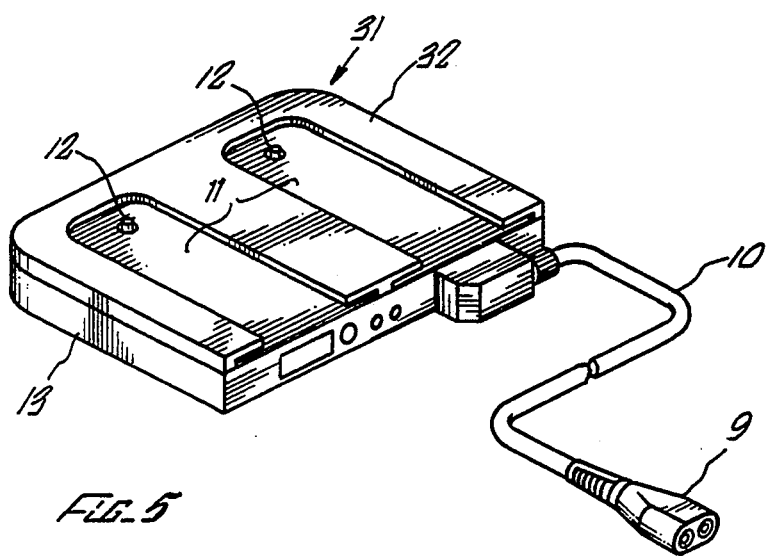
FIG. 5 is a drawing of a cabling system adapted for use with an electrode incorporating the teachings of the subject invention.

A cabelling system for coupling a pair of the electrodes to a defibrillator is illustrated in FIG. 5. As shown, this system comprises connector 9 for connecting the cabling system to connector 8 of the electrode pair. Also shown is cable 10, for coupling connector 9 (and therefore the pair of electrodes) to shock plate 31.

Shock plate 31 comprises a base 13 with member 32 placed over the base and configured to form defibrillator paddle wells 11, which in turn, are configured so that the defibrillator paddles fit snugly into the wells. Also shown are paddle contacts 12 situated in the wells for making electrical contact with the defibrillator paddles.

In operation, the following steps are performed with respect to the cabelling system of FIG. 5:

1. The operator selects the skin sites onto which the electrodes are to be applied.

2. The skin site is then prepared by cleaning and drying the skin with a rough cloth.

3. The peelable release liner is removed from the electrode pads and the adhesive side of the pads are rolled onto the skin of the patient.

4. When both electrodes are applied to the proper sites on the patient, the insulated wires 5a and 5b are connected to the cabling system by means of connectors 8 and 9, and the defibrillator paddles are placed in paddle wells 11.

5. If defibrillation or countershock is required, the defibrillator is charged as usual and a discharge is then initiated by depressing discharge switches on the defibrilator paddles, causing the defibrillator to discharge through the paddles and the cabling system into the electrodes.

Figure 6:
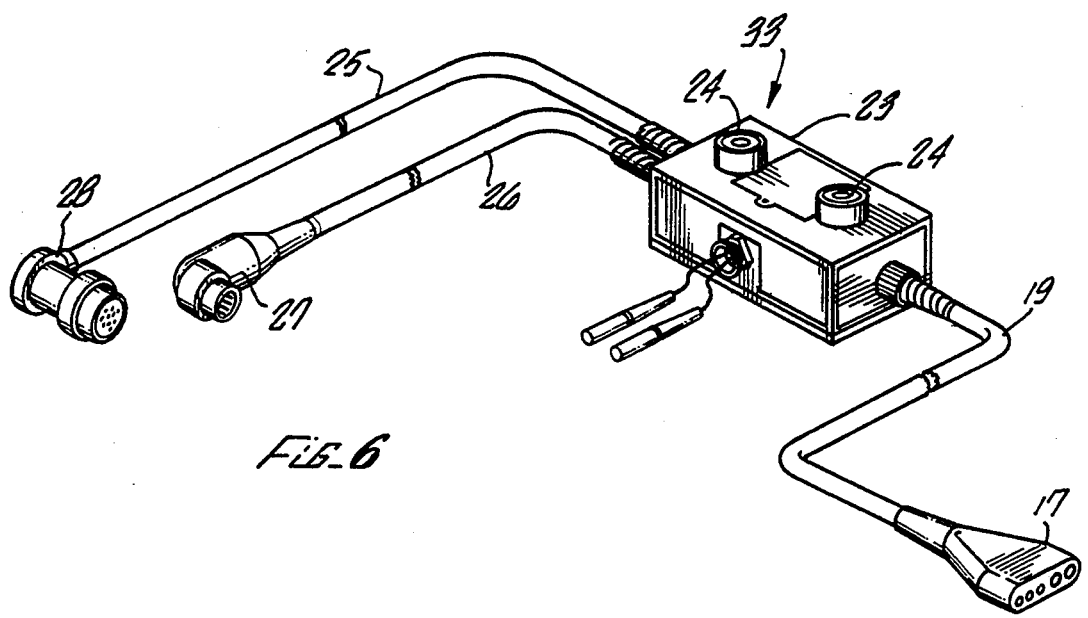
FIG. 6 is a drawing of an alternate cabling system adapted for use with an electrode incorporating the teachings of the subject invention.

An alternate cabling system for both defibrillating and monitoring the patient through the subject electrodes is illustrated in FIG. 6.

As illustrated, this cabling system comprises connector 17 adapted to couple to connector 8 of the electrode pair, and cable 19 for coupling the connector 17 (and therefore the pair of electrodes) to switch box 33.

Switch box 33 comprises a housing 23 and defibrillator buttons 24 for initiating defibrillation.

Coupled to the switch box are monitoring cable 25 and defibrillator cable 26. Also shown are defibrillation connector 28 for coupling the switch box to a defibrillator, and monitoring connector 27 for coupling the switch box to a monitor.

The switch box is configured to receive any electrical impulses originating from the patient through the electrodes (by means of connector 17 and cable 19), and delivering the same to monitoring cable 25, and is also configured to deliver any electrical impulses originating from a defibrillator through cable 26 to the electrodes through cable 19.

In operation, with respect to the cabelling system of FIG. 6, the first three steps described previously are performed, followed by the following steps:

4. When both electrodes are applied to the proper sites on the patient, the insulated wires 5a and 5b are connected to the cabelling system by means of connectors 8 and 17, and the cabelling system, in turn, is connected to a defibrillator and monitor by means of cables 25 and 26, and connectors 27 and 28.

5. ECG monitor signals obtained through the electrodes can then be observed by the operator on the monitor.

6. If defibrillation or countershock is required, the defibrillator is charged as usual and a discharge is initiated by pressing pushbuttons 24, which causes the defibrillator to discharge through the cabling system into the electrodes.

A cardiac system including the subject electrodes which allows for simultaneous pacing, defibrillation, and monitoring is illustrated in FIG. 3. In this configuration, it is preferable to use the pacing/defibrillation embodiment of the electrodes described previously in which the mesh backing is enclosed in a low impedance conductive rubber.

As shown in the figure, the system preferably comprises stimulating means 101, optional monitoring means 102, and electrode means 103. In the example of FIG. 3, stimulating means 101 further comprises defibrillator 201, defibrillator paddles 202, defibrillator input plates 203, and external pacemaker/defibrillator pass-through 204. As indicated, the defibrillator paddles are advantageously electrically coupled to the defibrillator, the defibrillator input plates are advantageously electrically coupled to the pass-through, which in turn, is advantageously electrically coupled to monitoring means. Finally, the electrode means is advantageously coupled to the pass-through.

In the example of FIG. 3, defibrillator 201 is a conventional defibrillator which delivers defibrillating energy by means of defibrillator paddles 202. In addition, monitoring means 102 is a conventional ECG monitor. Electrode means 103 is preferably a pair of non-invasive radiolucent electrodes incorporating the teachings of the subject invention.

Pass-through 204 is an external cardiac pacemaker that provides for the combined use of defibrillation and external cardiac pacing for emergency cardiac treatment. The device enables pacing or defibrillating current to be delivered through the electrodes. External cardiac pacing is an old and proven technique for initiating a heart contraction.

The defibrillator input plates located on the top of the pass-through are spring loaded and provide the ability to defibrillate and pace through the same set of electrodes. When one plate is depressed, an intermittent tone is sounded. When both plates are fully depressed, the tone becomes constant, indicating that both plates are down and that defibrillation may follow. Defibrillating energy is then generated and delivered by the defibrillator through the pass-through and to the patient through the electrodes. The plates are designed to be depressed by the paddles of any defibrillator with no gel required. After the plates have been depressed by means of the defibrillating paddles, the plates will spring back up and reconnect the pacemaker circuitry to the patient. When both plates are not fully depressed, pacing may follow. Pacing energy is then generated and delivered by the pass-through to the electrodes and ultimately the patient.

The pass-through also provides a connection for an optional two lead ECG monitor through the pass-through straight to the electrodes. If the monitor is added to the system, then the electrodes should be constructed with multiple pads in accordance with the teachings of U.S. Pat. Nos. 4,955,381 and 5,080,099, both of which are hereby fully incorporated by reference herein as though set forth in full. In this instance, the foil backings of the multiple pads should be replaced with the radiolucent backings of the subject invention.

The default mode of operation of the system is to pace the heart. As indicated above, the pass-through will generate and deliver external cardiac pacing energy through the electrodes to a patient automatically provided both input plates are not fully depressed. Should defibrillation be necessary, the paddles should be firmly pressed against the plates until both are depressed and the resultant tone is constant, and the defibrillator will generate and deliver defibrillating energy through the electrodes to the patient. Additional monitoring can also be optionally provided by the system in accordance with the teachings in U.S. Pat. Nos. 4,955,381 and 5,080,099.

It should be appreciated that additional advantages and modifications will readily occur to those skilled in the art. The invention in its broader aspects is not, therefore, limited to the specific details, representative methods, and illustrative examples shown and described. Accordingly, departures may be made from such details without departing from the spirit or scope of Applicant's general inventive concept. For example, other radiolucent backings are intended to be included within the scope of the subject invention besides a wire mesh backing. A tin or stainless steel backing which is thin enough to be radiolucent, for example, is also meant to be encompassed. Therefore, the invention is not intended to be limited except as by the appended claims.

What is claimed is:

1. A non-invasive radiolucent electrode comprising:
an adhesive conductive polymer pad having a first surface adapted for contacting a patient's skin, and having a second surface;
a stainless steel wire mesh backing to said pad configured to have between about 15 to 50 wires/inch and having wires with a diameter of between about 5 to 10 mils, the mesh having a front surface substantially covering the second surface of the pad, and having a back surface;

a plastic foam cover adapted to contact the back surface of the wire mesh backing and having a hole exposing at least a part of the wire mesh backing;

an insulated wire having a first exposed end which is adapted for insertion into the hole in the plastic foam cover, and electrically coupling to the exposed part of the wire mesh backing; and a wire retainer adapted to be placed over the hole in the plastic foam cover after the wire has been inserted, and adhered to the plastic foam cover.

2. A non-invasive radiolucent electrode comprising:

at least one pad having a first surface adapted to be placed in contact with a patient's skin, and having a second surface;

a conductive backing for the pad configured to be radiolucent and capable of conducting energy sufficient for defibrillation, and to substantially cover the second surface of the pad; and means for coupling said conductive backing to a source of energy.

3. The electrode of claim 2 wherein said backing is configured to be a wire backing having between about 15–50 wires/inch.

4. The electrode of claim 2 wherein said backing is configured to be a wire backing having between about 20–40 wires/inch.

5. The electrode of claim 2 wherein said backing is made of stainless steel.

6. The electrode of claim 2 wherein said backing is comprised of wires having a diameter of between about 5–10 mils.

7. The electrode of claim 2 wherein said backing is comprised of wires having a diameter less than about 9 mils.

8. The electrode of claim 2 wherein said backing has a percentage of open space which is greater than about 50%.

9. The electrode of claim 2 wherein said backing is embedded in a low-impedance conductive rubber.

10. The electrode of claim 2 wherein said backing has an outside edge which is covered by a mylar ring.

11. The electrode of claim 2 wherein the first surface of said pad has an area greater than about 25 sq. cm.

12. The electrode of claim 2 wherein said electrical coupling means is adapted to electrically couple said mesh backing to a defibrillator.

13. The electrode of claim 2 wherein said electrical coupling means is adapted to electrically couple said mesh backing to external pacing means.

14. The electrode of claim 2 wherein said electrical coupling means is adapted to electrically couple said mesh backing to an ECG monitor.

15. The electrode of claim 2 wherein said pad is made of a conductive polymer.

16. The electrode of claim 2 wherein said pad is made of hydrogel.

17. A cardiac system comprising:

at least a pair of electrodes wherein at least a first one of said electrodes is non-invasive, and wherein said first electrode comprises at least one pad having a first surface adapted to be placed in contact with a patient's skin, nd having a second surface, said electrode further comprising a conductive backing configured to be radiolucent and capable of conducting energy sufficient for defibrillation, and substantially cover said second surface of said pad;

a source of energy; and means for coupling said source to said backing.

18. The cardiac system of claim 17 wherein said source of energy comprises external pacing means for generating first electrical impulses adapted to pace the patient's heart.

19. The cardiac system of claim 17 wherein said source of energy comprises a defibrillator for generating second electrical impulses adapted to defibrillate the patient's heart.

20. The cardiac system of claim 19 wherein said defibrillator includes depressible defibrillator paddles adapted to externally deliver said second electrical impulses when the paddles are depressed and said coupling means includes a shock plate configured with paddle wells which are adapted so that said defibrillator paddles fit snugly into said wells.

21. The cardiac system of claim 19 wherein said coupling means further comprises:

a connector adapted to electrically couple said mesh backing to said defibrillator by bypassing any defibrillator paddles included in said defibrillator; and means for causing said defibrillator to externally deliver said second electrical impulses under operator control.

22. The cardiac system of claim 17 further comprising ECG monitoring means for receiving electrical impulses from the patient's heart, and said coupling means is further adapted to electrically couple said monitoring means to said backing.

23. The cardiac system of claim 17 wherein said source comprises:

external pacing means for producing first electrical impulses adapted to pace the patient's heart; and a defibrillator for producing second electrical impulses adapted to defibrillate the patient's heart;

wherein said coupling means further comprises means for delivering a selected one of said first and said second electrical impulses to said backing under operator control.

24. The cardiac system of claim 23 further comprising ECG monitoring means for receiving electrical impulses from the patient's heart, wherein said electrical coupling means is further adapted to couple said monitoring means to said mesh backing.

25. A process for stimulating a patient's heart utilizing a non-invasive radiolucent electrode comprising the steps of:

configured the electrode to have at least one pad;

contacting the patient's skin with a first surface of said at least one electrode pad, said at least one pad also having a second surface;

substantially covering the second surface of the at least one pad with a conductive backing configured to be radiolucent and capable of conducting defibrillating energy;

delivering energy to the backing of the at least one pad; and imaging any of the patient's internal organs while said first surface of said at least one pad is contacting the patient's skin.

26. The process of claim 25 wherein said delivering step comprises delivering electrical impulses adapted to defibrillate the patient's heart to the backing of the at least one pad.

27. The process of claim 25 wherein said delivering step comprises delivering electrical impulses adapted to pace the patient's heart to the backing of the at least one pad.

28. The processes of claim 25 further comprising receiving electrical impulses from the patient's heart through said mesh backing for use in ECG monitoring.

29. The process of claim 25 further comprising the step of configuring said backing to be a wire backing having between about 15–50 wires/inch.

30. The process of claim 25 further comprising the step of configuring said backing to be a wire backing having between about 20–40 wires/inch.

31. The process of claim 25 further comprising the step of configuring said backing to be made of stainless steel.

32. The process of claim 25 further comprising the step of configuring said backing to a wire backing comprising wires having a diameter of between about 5–10 mils.

33. The process of claim 25 further comprising the step of configuring said backing to comprise a wire backing comprising wires having a diameter of less than about 9 mils.

34. The process of claim 25 further comprising the step of configuring said backing to have a percentage of open space of greater than about 50%.

35. The process of claim 25 further comprising the step of embedding the backing in a low-impedance conductive rubber.

36. The process of claim 25, wherein said backing has an outside edge, further comprising covering the outside edge with a mylar ring.

37. The process of claim 25 further comprising configuring the first surface of said pad to have an area greater than about 25 sq. cm.

38. A process comprising the steps of:
providing a non-invasive radiolucent electrode capable of conducting defibrillating energy and having at least one pad;
contacting a patient's skin with a surface of said pad;
delivering electrical impulses, determined appropriate to defibrillate the patient's heart, to said patient through said pad; and
imaging any of the patient's internal organs while said pad is contacting the patient's skin.

* * * * *